US008388674B2

(12) United States Patent
Sandhu et al.

(10) Patent No.: US 8,388,674 B2
(45) Date of Patent: Mar. 5, 2013

(54) CONFORMABLE STENTS AND METHODS FOR MAKING (75) Inventors: Gurpreet S. Sandhu, Rochester, MN (US); Dan Dragomir Daescu, Rochester, MN (US); Charanjit S. Rihal, Rochester, MN (US); Samuel J. Asirvatham, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 79 days.

(21) Appl. No.: 12/919,122

(22) PCT Filed: Feb. 25, 2009

(86) PCT No.: PCT/US2009/035139
§ 371 (c)(1),
(2), (4) Date: Aug. 24, 2010

(87) PCT Pub. No.: WO2009/108699
PCT Pub. Date: Sep. 3, 2009

(65) Prior Publication Data
US 2010/0331809 A1    Dec. 30, 2010

Related U.S. Application Data (60) Provisional application No. 61/031,145, filed on Feb. 25, 2008.

(51) Int. Cl.
*A61F 2/82*    (2006.01)
*A61F 11/00*    (2006.01)

(52) U.S. Cl. ......... 623/1.15; 623/1.11; 606/108
(58) Field of Classification Search .......... 623/1.1–1.15; 606/108; *A61F 2/06*
See application file for complete search history.

(56) References Cited

U.S. PATENT DOCUMENTS

| 4,687,808 | A | 8/1987 | Jarrett et al. |
| 5,716,410 | A | 2/1998 | Wang et al. |
| 6,007,575 | A | 12/1999 | Samuels |
| 6,281,263 | B1 | 8/2001 | Evans et al. |
| 7,255,874 | B1 | 8/2007 | Bobo et al. |
| 2005/0187561 | A1* | 8/2005 | Lee-Sepsick et al. ........ 606/108 |
| 2006/0182873 | A1 | 8/2006 | Klisch et al. |
| 2006/0184112 | A1 | 8/2006 | Horn et al. |
| 2007/0027524 | A1* | 2/2007 | Johnson et al. ............. 623/1.11 |
| 2011/0054347 | A1* | 3/2011 | Goss et al. .................... 600/562 |

FOREIGN PATENT DOCUMENTS

| WO | WO96/18427 | 6/1996 |
| WO | WO98/40033 | 9/1998 |
| WO | WO2007/089762 | 8/2007 |

OTHER PUBLICATIONS

"Biocompatible/Biodegradable Materials," Aldrich Catalog, as early as Apr. 19, 2006, pp. 18-45.

(Continued)

*Primary Examiner* — Thomas J Sweet
*Assistant Examiner* — Jason-Dennis Stewart
(74) *Attorney, Agent, or Firm* — Fish & Richardson P.C.

(57) ABSTRACT

Materials and methods for making conformable stents. The stents can be generated by, for example, injecting a fluid into a scaffold on the outer surface of an angioplasty balloon inflated at the site of a stenosis, and allowing the fluid to harden or set, thus generating a stent that can remain in the vessel at the site of stenosis.

17 Claims, 10 Drawing Sheets

OTHER PUBLICATIONS

Kirby and Goodwin, "Treatment of a primary type IA endoleak with a liquid embolic system under conditions of aortic occlusion," *J. Vasc. Surg.*, 2003, 37:456-460.

Klisch et al., Combined stent implantation and embolization with liquid 2-polyhydroxyethyl methacrylate for treatment of experimental canine wide-necked aneurysms, *Neuroradiology*, 2002, 44:503-512.

Washburn et al., "Co-extrusion of biocompatible polymers for scaffolds with co-continuous morphology," *J. Biomed. Mater. Res.*, 2002, 60:20-29.

International Search Report and Written Opinion of the International Searching Authority in International Application No. PCT/US2009/035139, mailed Oct. 1, 2009, 10 pages.

International Preliminary Report on Patentability in International Application No. PCT/US2009/035139, mailed Sep. 10, 2010, 5 pages.

Extended European Search Report in European Application No. 09714651.8, dated Sep. 25, 2012, 7 pages.

\* cited by examiner

CONFORMABLE STENTS AND METHODS FOR MAKING

CROSS-REFERENCE TO RELATED APPLICATIONS

This application is a National Stage application under 35 U.S.C. §371 of International Application No. PCT/US2009/035139 having an International Filing Date of Feb. 25, 2009, which claims benefit of priority from U.S. Provisional Application Ser. No. 61/031,145, filed on Feb. 25, 2008.

TECHNICAL FIELD

This document relates to materials and methods for treating sites of stenosis in bodily vessels (e.g., blood vessels).

BACKGROUND

Angioplasty is the mechanical widening of a narrowed blood vessel or a blood vessel that has become obstructed due to, for example, atherosclerosis. The term "angioplasty" has come to include all manner of vascular interventions typically performed in a minimally-invasive or "percutaneous" method.

Coronary angioplasty, also referred to as percutaneous coronary intervention, is a therapeutic procedure to treat stenotic (narrowed) coronary arteries of the heart found in coronary heart disease. These stenotic segments can result from the build-up of cholesterol-laden plaques that form due to atherosclerosis. Coronary angioplasty typically is performed by an interventional cardiologist.

Peripheral angioplasty refers to the use of mechanical widening to open blood vessels other than the coronary arteries. This procedure often is referred to as percutaneous transluminal angioplasty, or PTA. PTA is most commonly performed to treat narrowing in the leg arteries, especially the common iliac, external iliac, superficial femoral, and popliteal arteries. PTA also can be used to treat narrowing of veins. In addition, atherosclerotic obstruction of the renal artery and carotid artery stenosis can be treated with angioplasty.

Any of these angioplasty procedures can include placement of a stent to prevent or counteract constriction of localized blood flow. The stent can act as a scaffold, remaining in place permanently to help keep the vessel open. A stent typically is inserted through a main artery in the groin (femoral artery) or arm (brachial artery) on a wire or catheter (e.g., a balloon catheter, in the case of balloon angioplasty), and threaded up to the narrowed section of the vessel. In a balloon angioplasty procedure, the balloon can be inflated to push the plaque out of the way and expand the vessel. In a balloon angioplasty/stent placement procedure, a stent either can be stretched open by the balloon at the same time as the artery, or can be inserted into the vessel immediately after the angioplasty procedure. Once in place, the stent helps to hold the vessel open, thus improving blood flow. In addition, since angioplasty can result in tears or dissections in the intimal lining of blood vessels, stents can push back these flaps of tissue and thereby maintain vessel patency.

SUMMARY

This document is based in part on the discovery that stents can be formed in blood vessels by injecting a fluid substance at the site of a stenosis and allowing the substance to harden. Thus, this document provides materials and methods for making and placing stents in narrowed or obstructed vessels (e.g., blood vessels) at the site of stenosis. The stents made by the methods provided herein can conform to irregularly shaped areas within vessels at the site of narrowing or obstruction. Such stents can be particularly useful, for example, at sites where a vessel is of non-uniform diameter. Such stents also can be particularly useful at bifurcations, where a narrowing or obstruction occurs at a branch between two vessels.

In one aspect, this document features a method for making a stent, comprising: a) inserting into a bodily vessel a balloon having an outer surface, wherein said outer surface defines one or more grooves configured to form a scaffold for a stent; b) inflating the balloon at the site of a stenosis within the vessel; c) injecting a fluid substance into the one or more grooves; d) allowing the fluid substance to harden; and e) deflating the balloon and removing it from the vessel. The one or more grooves can be configured to form a mesh pattern scaffold, a helical or coiled scaffold for a stent, or a scaffold of connected rods for a stent. The one or more grooves can define a lumen that is entirely contained within the wall of the balloon. The outer surface of the balloon and the surface of the one or more grooves can have a covering that is separate from the balloon wall. The balloon wall and the covering can comprise different materials, or the balloon wall and the covering can comprise the same materials. Each of the one or more grooves can have a separate covering, wherein each of the separate coverings defines a lumen extending along the outer surface of the balloon. Each of the lumens can have a triangular cross-section. The injected substance can be selected from the group consisting of hydrogels, homopolymers, and copolymers. The injected substance can be selected from the group consisting of modified cellulose, cellulosic derivatives, and polymers of hydroxyethyl methacrylate, glycidyl methacrylate, glycidyl methacrylate/N-vinyl pyrrolidone/hydroxyethyl methacrylate, 2-polyhydroxyethyl methacrylate, n-butyl cyanoacrylate, co-extrusions of poly(∈-caprolactone) and poly(ethylene oxide), cellulose acetates, ethylene vinyl alcohol copolymers, acrylics, polyacrylonitrile, hydroxyalkyl acrylates, hydroxyalkyl methacrylates, epoxy acrylates, epoxy methacrylates, amino alkyl acrylates, amino alkyl methacrylates, N-vinyl compounds, amino styrenes, polyvinyl alcohols, polyvinyl amines, polyacrylamide, polysaccharides, modified polysaccharides, polyethylene glycol, polypropylene glycol, vinyl pyridine, vinyl sulfonate, polyvinyl sulfate, vinylene carbonate, vinyl acetic acid, vinyl crotonic acid, allyl amines, allyl alcohols, vinyl glycidyl ether, and allyl glycidyl ether. The injected substance can harden at bodily temperature. The method can further comprise injecting a curing agent.

In another aspect, this document features a stent that is generated in situ according to a method as described herein. The stent can have a mesh configuration, a helical or coiled configuration, can comprise a series of connected rods, or can define a hollow cylinder with solid walls. The stent can comprise a material selected from the group consisting of hydrogels, homopolymers, and copolymers. The stent can comprise a material selected from the group consisting of modified cellulose, cellulosic derivatives, and polymers of hydroxyethyl methacrylate, glycidyl methacrylate, glycidyl methacrylate/N-vinyl pyrrolidone/hydroxyethyl methacrylate, 2-polyhydroxyethyl methacrylate, n-butyl cyanoacrylate, co-extrusions of poly(∈-caprolactone) and poly(ethylene oxide), cellulose acetates, ethylene vinyl alcohol copolymers, acrylics, polyacrylonitrile, hydroxyalkyl acrylates, hydroxyalkyl methacrylates, epoxy acrylates, epoxy methacrylates, amino alkyl acrylates, amino alkyl methacrylates, N-vinyl compounds, amino styrenes, polyvinyl alcohols, polyvinyl amines, polyacrylamide, polysaccharides, modified polysaccharides, polyethylene glycol, polypropylene glycol, vinyl pyridine, vinyl sulfonate, polyvinyl sulfate, vinylene carbonate, vinyl acetic acid, vinyl crotonic acid, allyl amines, allyl alcohols, vinyl glycidyl ether, and allyl glycidyl ether.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3A depicts a configuration in which the lumen of the channels is entirely within the balloon wall. FIG. 3B depicts a configuration in which the outer surface of the balloon, including the surface of the grooves, has a covering that is separate from the balloon wall. FIG. 3C depicts a configuration in which each groove has a separate covering that completely surrounds the lumen into which the stent substance will be injected.

In FIG. 4A, a balloon is inserted into a vessel and inflated at a site of stenosis. A liquid or gelatinous substance is then injected into a groove on the outer surface of the balloon (FIG. 4B) until it reaches the distal end of the balloon (FIG. 4C).

In FIG. 5A, a liquid or gelatinous substance is injected through a first port (arrow a) into a groove on the outer surface of a balloon, while suction is applied to a second port (arrow b) to draw the substance along the channel. In FIG. 5B, once a sufficient amount of substance has been injected, suction is applied at the second port (arrow b) to draw the substance through the groove.

Like reference symbols in the various drawings indicate like elements.

DETAILED DESCRIPTION

Figure 1A:
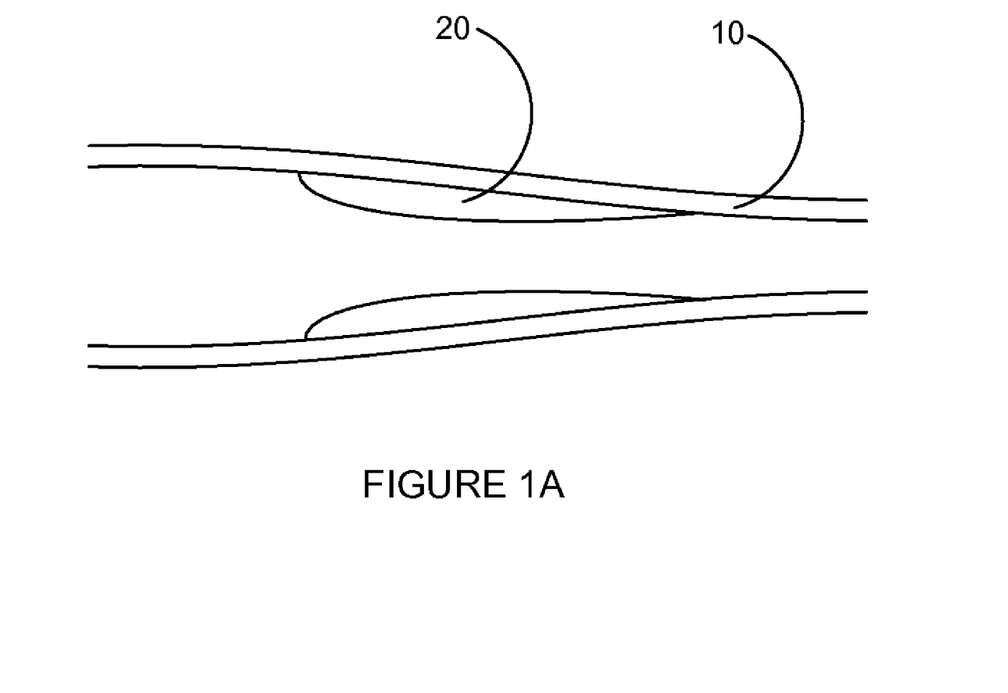
FIG. 1A is a cross-sectional view of a blood vessel having a plaque therein.
Figure 1B:
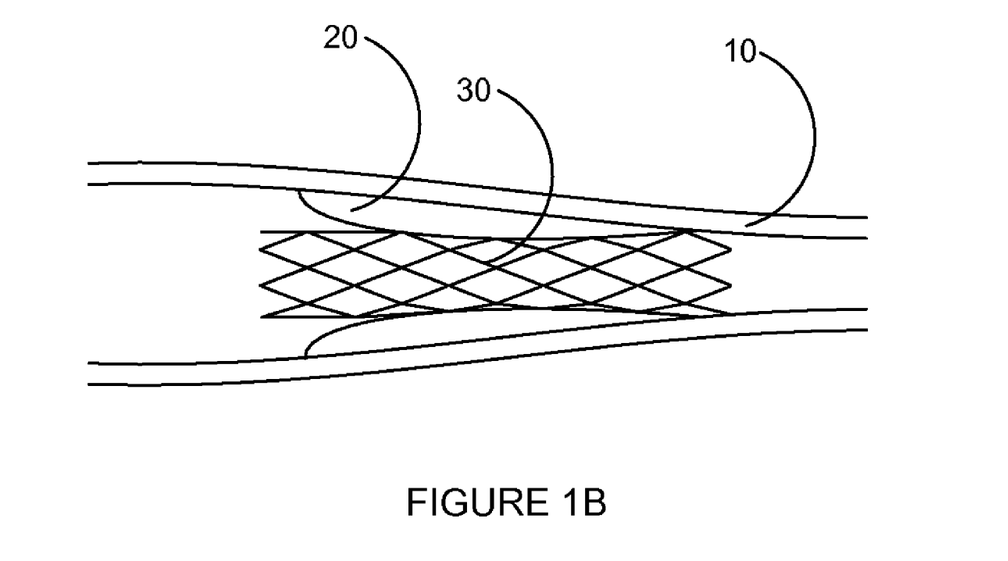
FIG. 1B is a cross-sectional view of the blood vessel after placement of a stent.

Materials and methods for making conformable stents are provided herein. A conformable stent can be generated by, for example, injecting a fluid substance (e.g., a liquid or gelatinous substance) at the site of a narrowing or obstruction in a vessel and allowing the fluid to set, resulting in a rigid form that can maintain the vessel in an open state. As shown in FIG. 1A, for example, vessel 10 can have an area of stenosis caused by plaque 20. Stent 30, depicted in FIG. 1B, can be placed at the site of plaque 20 to hold vessel 10 in an open state, thus facilitating blood flow.

In general, a stent as provided herein can be constructed on the outside of a balloon that has been deployed into a vessel and inflated at a site of stenosis, wherein a fluid substance is then injected into a scaffold of one or more channels defined on the outer surface of the balloon. The injected substance can be in a liquid state as it is applied to the scaffold, and can solidify after a period of time. Once the fluid has been injected and allowed to set, the balloon can be deflated and removed to leave the "conformed" stent in place, thus holding the stenotic portion of the vessel in an open state.

Stents deployed as described herein can be useful to treat sites where a vessel is of non-uniform diameter, and lesions at arterial branch points (e.g., ostial lesions or bifurcated lesions). The methods provided herein also can be useful to address situations where a stenotic lesion is found at the ostium of the branch of a main vessel with the main vessel itself being normal, where lesions are found in both the main vessel and the branch, and where there is multiple branching of a vessel.

In some embodiments, a balloon having preformed channels on its outer surface can be inserted into a long arterial segment with stenosis, into a vessel with a branch at the site of stenosis, or into a bifurcating vessel with stenosis. The balloon can be deployed (e.g., inflated with a fluid), and a substance can be injected into the preformed channels on the surface of the balloon to form the matrix for a stent that fits precisely into the vessel, including any branch or bifurcation site. Such stents can be particularly useful in situations where there is significant disparity between the diameter of the vessel proximal and distal to the stenotic segment, but they also can be useful in other situations as noted above, for example. The approach described herein can avoid issues such as, e.g., the need to use differently sized stents at different segments of a vessel.

Figure 2A:
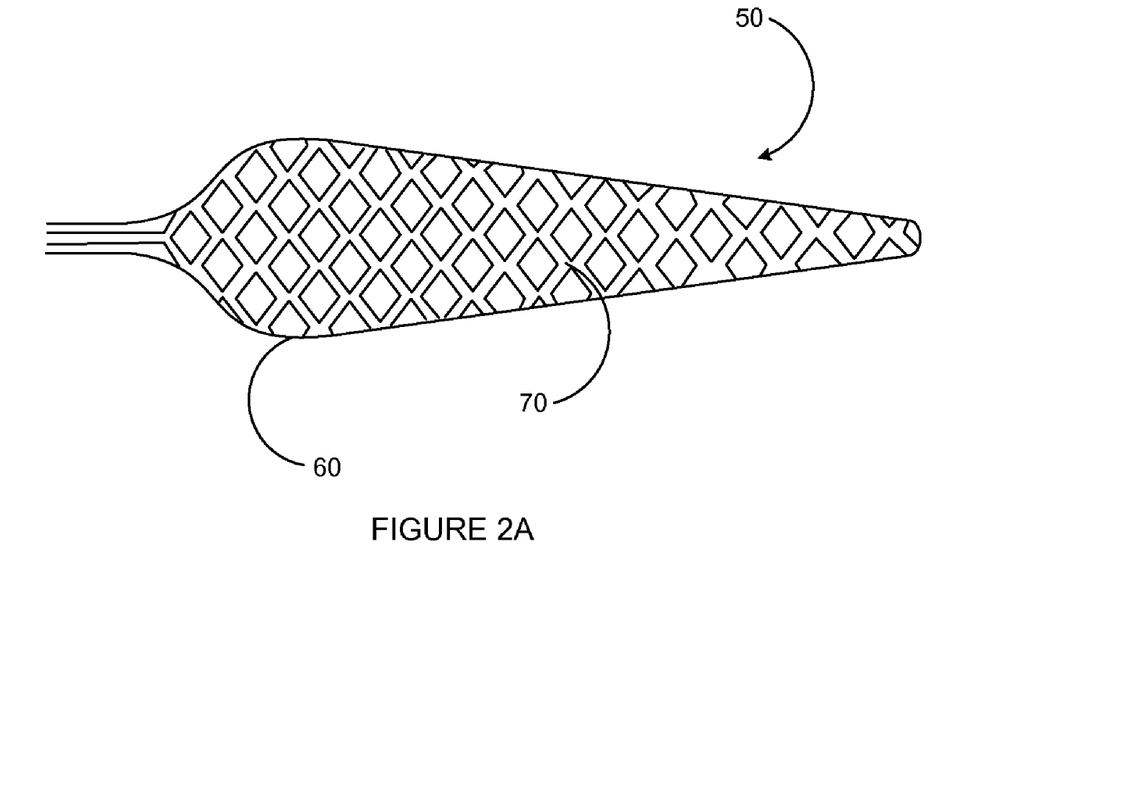
FIGS. 2A-2F are drawings of an inflated angioplasty balloon having one or more grooves in various configurations on its outer surface. The groove(s) can define different patterns, including a mesh (FIG. 2A), a coil (FIG. 2B), a double coil (FIG. 2C), a double helix (FIG. 2D), and a series of connected rods (FIG. 2E). The balloon depicted in FIG. 2F has an indentation around much of its outer surface, such that it can be used to generate a tubular stent having essentially solid walls.
Figure 2B:
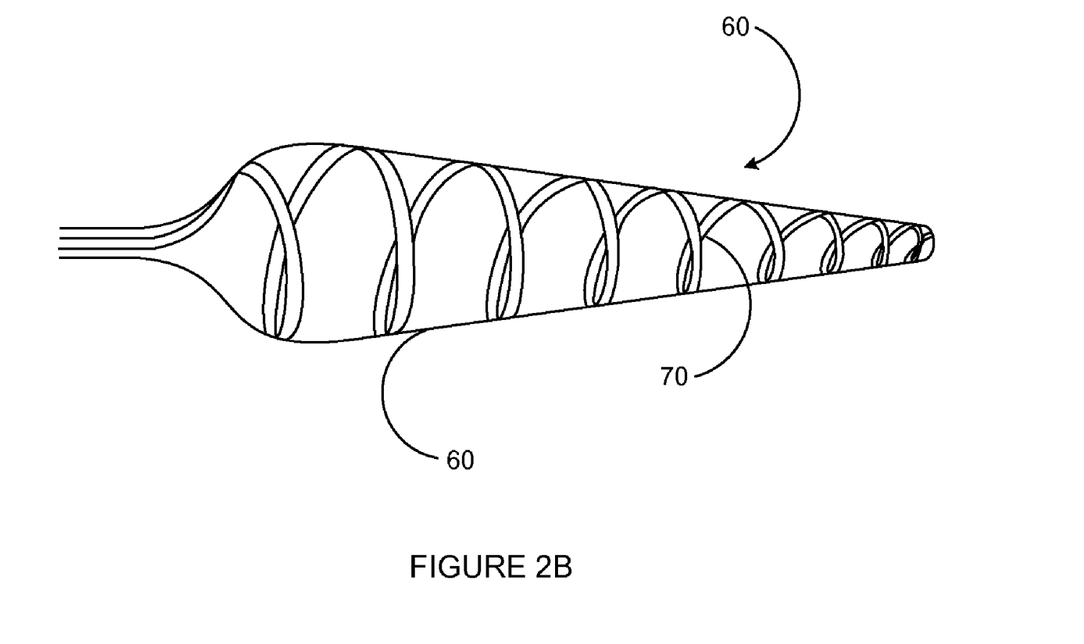
Figure 2C:
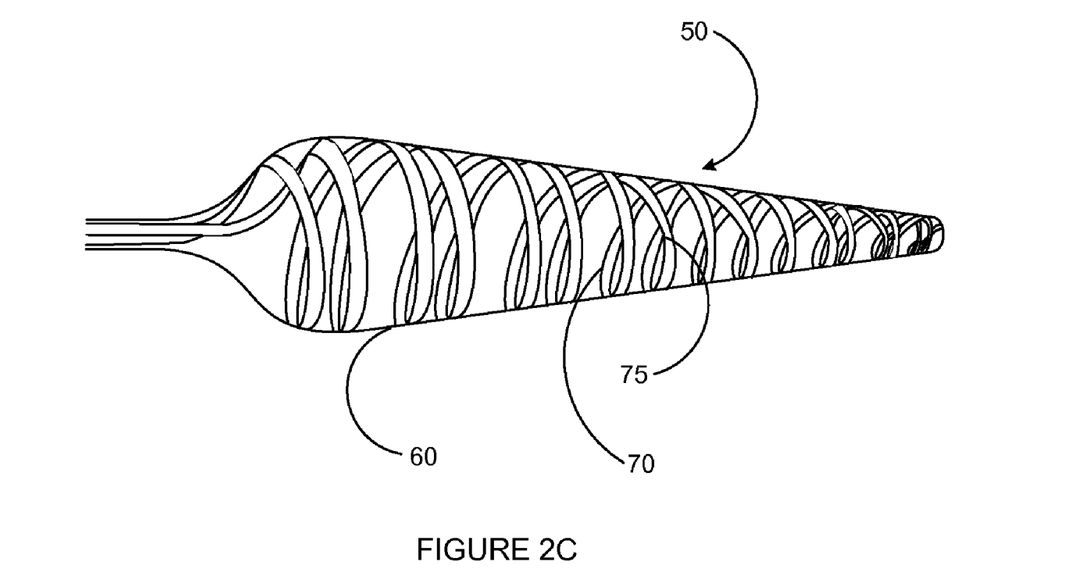
Figure 2D:
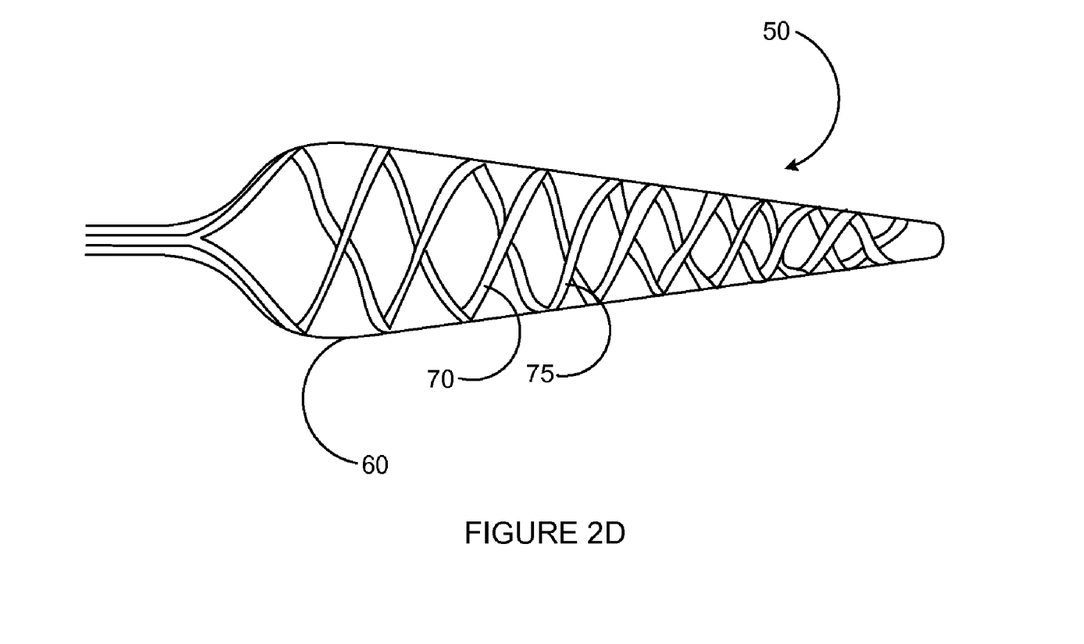
Figure 2E:
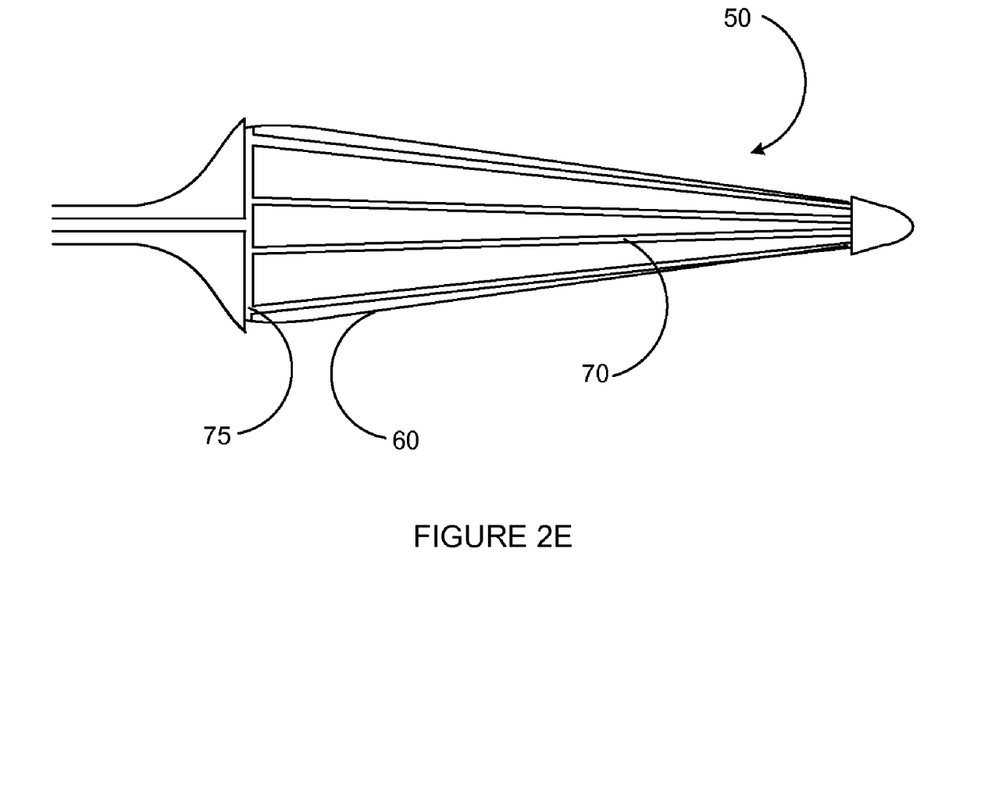
Figure 2F:
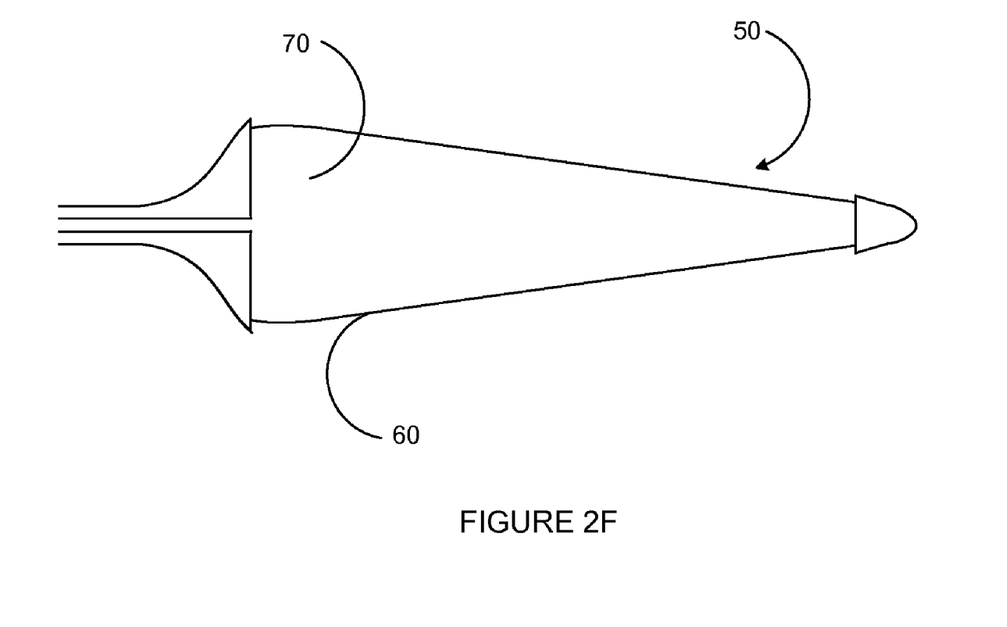

This document provides balloons for use in the methods described herein. A balloon can be, for example, essentially a standard angioplasty balloon, with one or more grooves or channels on its outer surface. The one or more grooves or channels can have any configuration, and can define any pattern on the surface of the balloon. For example, a channel can have a cross-section that is circular, semi-circular, triangular, square, rectangular, or any other shape. FIGS. 2A-2E depict examples of balloon 50 with outer surface 60, where outer surface 60 has grooves 70 and 75, where applicable, defining a stent scaffold thereon. The scaffold can have a configuration that will result in a stent having a mesh pattern (FIG. 1B), a honeycomb pattern (FIG. 2A), a coil or double coil pattern (FIGS. 2B and 2C, respectively), a double helix pattern (FIG. 2D), or a connected rod pattern (FIG. 2E). FIG. 2F shows an example of an embodiment in which nearly the entire outer surface of balloon 50 is recessed, such that it can be used to generate a stent that is essentially a hollow tube with solid walls. In some embodiments, a balloon can have two or more grooves that are in fluid communication with separate injection ports. Such balloons can be used to generate stents having two or more sections that contain different materials, for example.

A balloon can be made from any material. A balloon (e.g., the wall of a balloon) can include, for example, one or more polymers (e.g., a mixture of polymers). For example, a balloon can include one or more thermoplastics (e.g., polyolefins, polyamides such as nylon, polyesters such as polyethylene terephthalate, polybutylene terephthalate, polyethylene naphthalate, and polytrimethylene terephthalate, polyethers, polyurethanes, polyvinyls, polyacrylics, fluoropolymers, copolymers and block copolymers thereof, and mixtures thereof) and/or one or more thermosets (e.g., elastomers such as EPDM, epichlorohydrin, polyureas, nitrile butadiene elastomers, silicones, epoxies, and isocyanates). Examples of biocompatible thermosets include biodegradable polycaprolactone, poly(dimethylsiloxane) containing polyurethanes and ureas, and polysiloxanes. Other examples of polymers that can be used in balloons include polyimides, polyethylenes, polyethylene ionomers, polyethylene copolymers, polyetheretherketone, thermoplastic polyester elastomers, and combinations thereof. A balloon can be formed using any suitable method, including, without limitation, blow molding, film molding, injection molding, and/or extrusion. In some embodiments, for example, a polymer tube can be extruded and then stretched and blown to form a balloon. After a balloon has been formed, it can be attached to a catheter shaft by laser bonding or any other suitable technique.

Any suitable method can be used to create one or more grooves or channels in the wall of a balloon, including methods known in the art. For example, a balloon can be formed and then stretched and inflated, and grooves can thereafter be ablated into the wall. In some embodiments, grooves or channels can be ablated into the surface of a balloon that has not been inflated. Such grooves can be formed, for example, by laser ablation.

The preformed channels on the exterior of the balloon should not "break away" or embolize distally in the vessel after a substance has been injected to form a stent and the balloon is deflated. Thus, in some embodiments, the balloons provided herein can have a free margin (i.e., the surface between the channels on the exterior of the balloon and the vessel wall) that is covered. In some cases, for example, the same substance that is used to form the stent matrix can be present as the "roof" of the channels on the outer surface of the balloon. Since this substance is solid at body temperature, deployment of the balloon can bring the substance into contact with the vessel wall. A liquid or gelatinous form of the same substance then can be injected to fill the channel, thus strengthening the matrix and forming a stent. In some cases, the "roof" of the channels on the balloon exterior can comprise a material that is different from the balloon, the matrix, or the rest of the stent. Such substances typically can stretch as the balloon is inflated. As in the above case, when a liquid/gelatinous substance is injected into the channels and solidifies, the "roof" can stay in contact with the blood vessel wall when the balloon is deflated and removed from the vessel, leaving the stent behind. The roof also can be designed to precisely tear away at a single pre-scored line so that it completely detaches from the stent and is fully removed when the balloon is deflated and withdrawn.

Figure 3A:
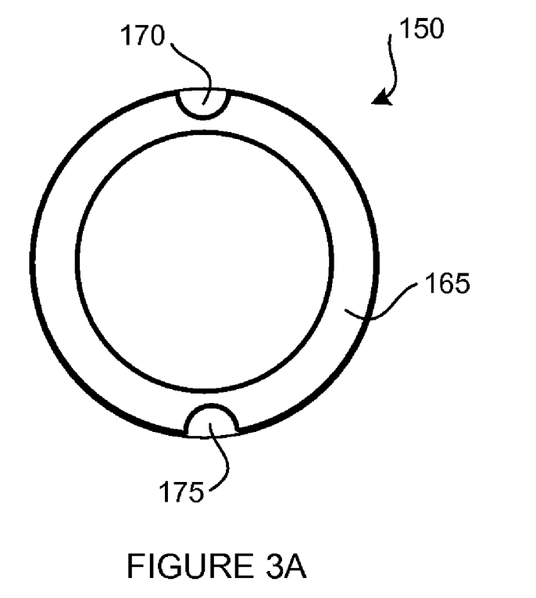
FIGS. 3A, 3B, and 3C are drawings showing cross-sections through balloons having grooves/channels defined in the walls thereof.
Figure 3B:
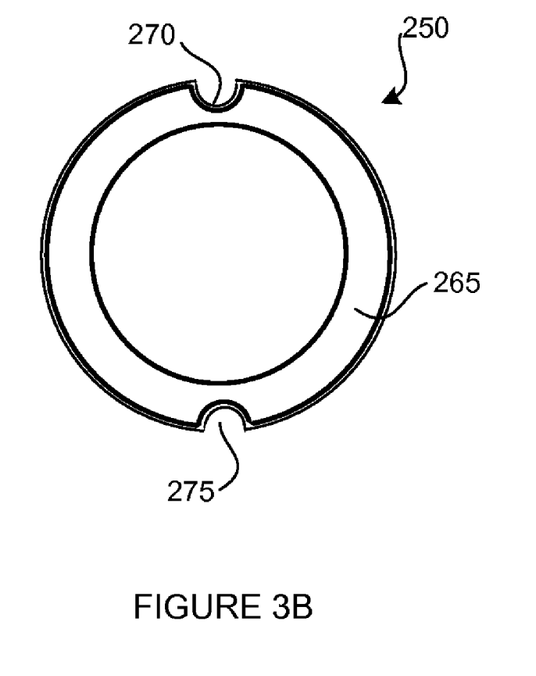
Figure 3C:
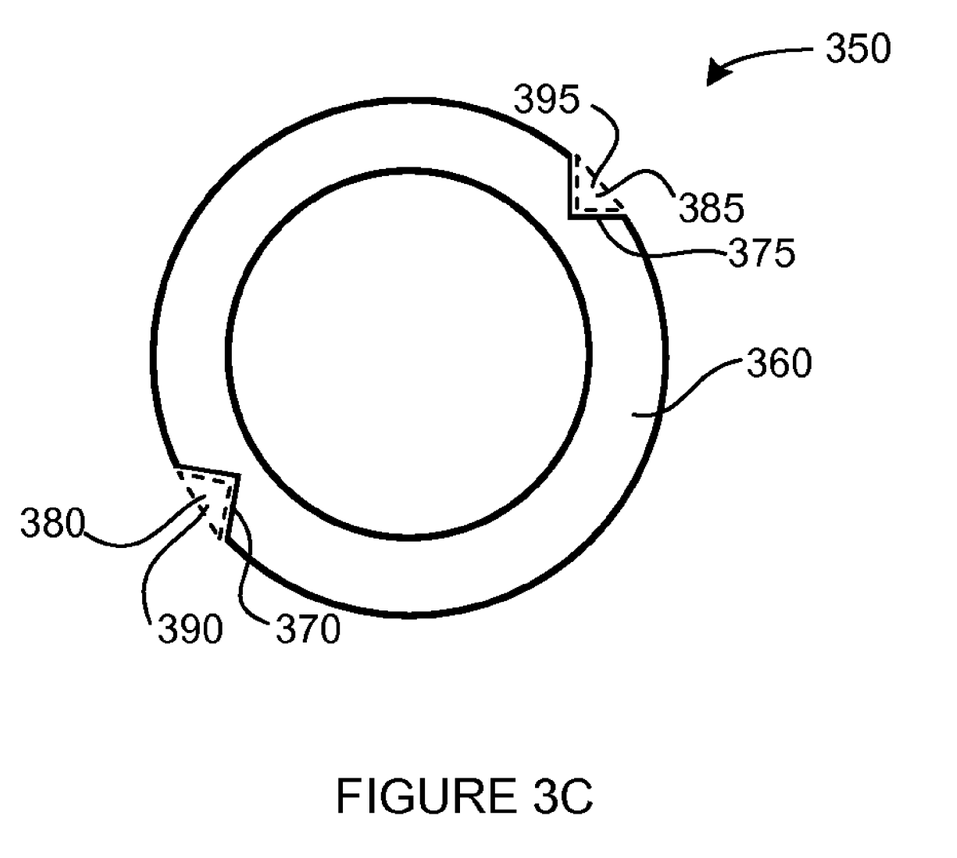

FIGS. 3A to 3C show cross-sections through a balloon, depicting several options for how the grooves of a stent scaffold can be configured. As shown in FIG. 3A, for example, the entire cross-section of the lumens defined by channels 170 and 175, through which the stent substance is injected, can be defined by wall 165 of balloon 150. In such a configuration, at no time will a substance injected into the scaffold come directly into contact with the vessel wall. Once the compound solidifies and forms a "solid" stent, the balloon can be deflated and the stent can be left in place. In these embodiments, the material used to cover the channel on the balloon can be made of any suitable biocompatible substance, since it will be in contact with body tissue. In addition, the material can be perforated or scored to more efficiently separate it from the rest of the balloon during deflation. The covering material can provide an additional benefit of protecting vessel tissue from the injected substance. In some embodiments, the covering material can be biodegradable.

FIG. 3B illustrates an embodiment in which no part of balloon 250 is left behind in the vessel after deflation, and the lumen is formed partly as "etchings" or grooves 270 and 275 in wall 265 of balloon 250, with the vessel wall itself serving as the "roof" of the channel once balloon 250 has been inflated.

FIG. 3C depicts an embodiment with balloon 350 having wall 365 that defines grooves 370 and 375, and coverings 380 and 385 that define lumens 390 and 395. Lumens 390 and 395 are partially defined by the sides of grooves 370 and 375. Coverings 380 and 385 cover not only the vessel-facing surfaces of grooves 370 and 375, but also define a "roof" for lumens 390 and 395. In such embodiments, all of the injected stent-forming substance can be kept away both from the vessel wall and the contents of the vessel, since all of the injected substance is encased in the material of coverings 380 and 385. In contrast, in the embodiment depicted in FIG. 3A, the injected substance can be exposed to vessel contents.

In some embodiments, as depicted in FIG. 3C, for example, balloon 350 can have a groove (e.g., groove 370 and/or groove 375) on its outer surface, with a covering over only the groove (e.g., covering 380 and/or 385) that defines a triangular lumen. In some cases, the lumen itself can be made of the same substance that is to be injected to form the stent, but can have slightly different physical characteristics such that it is solid and expandable at room temperature as well as at body temperature. The remainder of the balloon material interface can be perforated so that when the balloon is deflated, it tears away from the triangular lumen that has been filled with the injected compound. The cleavage plane can be important in the sense that if the lumen is made of the balloon material (i.e., if all of the lumen is made from the same material as the balloon), the chances of material tearing away may be increased. In such cases, the material comprised by the balloon should be non-thrombotogenic, while the thrombogenicity of the substance injected into the lumen may be less important since it will be entirely contained within the lumen.

Balloons useful in the presently described devices and methods typically are conformable and of relatively low pressure, but may be capable of providing different pressures at different sites. The balloons also may be relatively long, and can retain their essentially cylindrical shape even at branch points and within other complex vascular architecture. Any suitable method can be used to make a balloon having one or more grooves on its outer surface, with or without a covering as described above. Such methods are set forth, for example, in U.S. Patent Publication Nos. 2006/0184112 and 2006/

0182873, which are incorporated herein by reference in their entirety. A balloon can be formed by, for example, injection molding, blow molding, film molding, or extrusion. Once formed, a balloon can be attached to a catheter shaft using any suitable method (e.g., laser bonding). Any suitable methods also can be used to form one or more grooves on the outer surface of a balloon, and to generate a covering over the balloon and/or the grooves. For example, laser ablation (e.g., using UV light) can be used to form one or more grooves in predetermined areas on the outer surface of a balloon. Methods that can be used to form a coating or covering over a balloon and/or the grooves thereon include, for example, dipping, spraying, and/or dispensing.

Figure 4A:
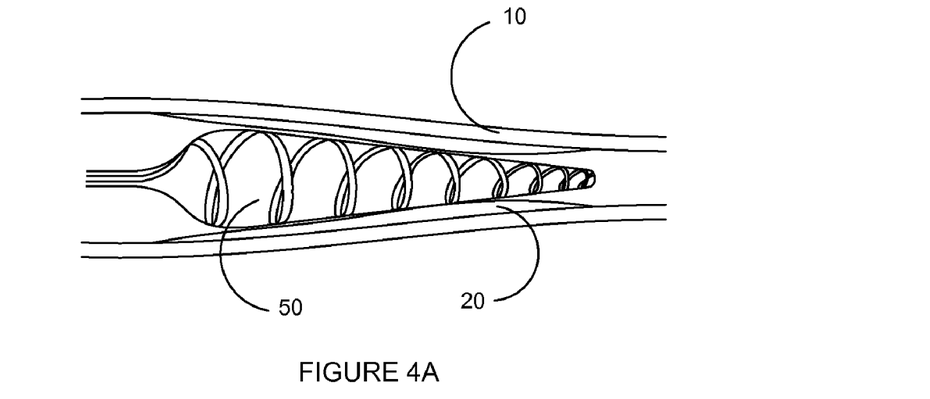
FIGS. 4A-4C are drawings illustrating a method as described herein.
Figure 4B:
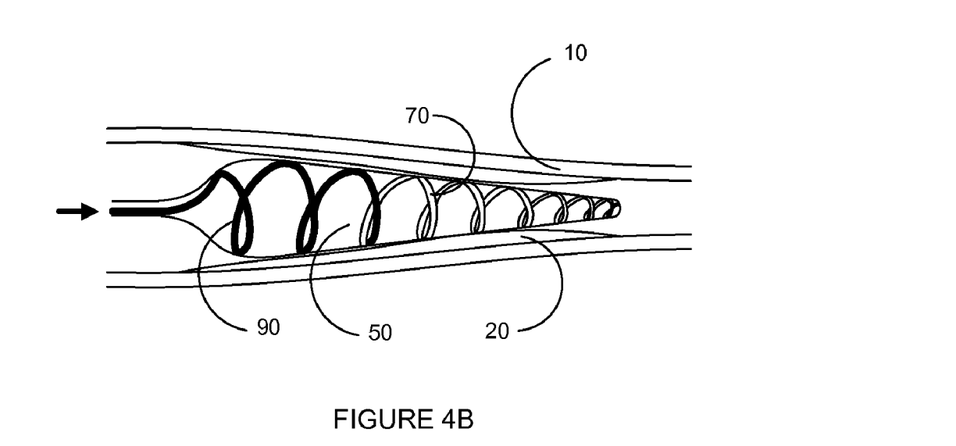
Figure 4C:
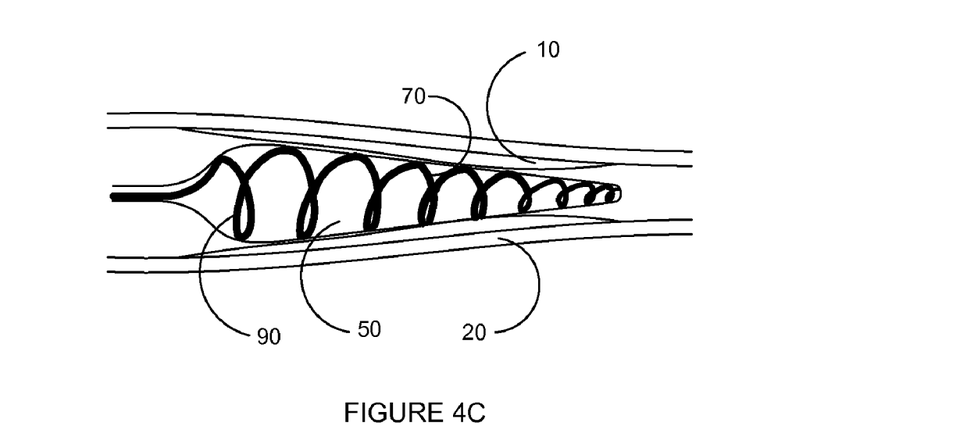

FIGS. 4A to 4C provide a general illustration of the methods for making stents as provided herein. As shown in FIG. 4A, balloon 50 can be inserted into narrowed vessel 10 at the site of a plaque 20, and can conform to the shape of vessel 10 upon inflation. FIGS. 4B and 4C depict substance 90 being injected into groove 70 on the exterior surface of balloon 50, until substance 90 reaches the tip of balloon 50. FIGS. 4A-4C portray generation of a relatively simple, coil-like stent, but again, the groove(s) on the outer surface of a balloon can have any suitable configuration and can be designed to result in a stent of any type (e.g., an interwoven or intermeshing type stent, a stent defining a hollow tube with solid walls, or a stent having a honeycomb pattern, a coil, a helix, or connected rods).

Any suitable substance can be used to form a stent as described herein. Substances that are useful in the methods provided herein typically have one or more of the following characteristics: inert with regard to bodily fluids/materials; non-thrombogenic; solid at body temperature; liquid or gelatinous at either higher than body or lower than body temperature; made of a dielectric or electrically conducting structure as compatible with common antiplatelet and other drugs; and non-toxic/biocompatible. Biocompatible polymers that can be used to generate stents as described herein include, for example, the polymers disclosed in U.S. Pat. No. 6,281,263, which is incorporated herein by reference in its entirety. In some embodiments, the stent material can have properties that allow for reversal of its physical state (e.g., properties that allow the material of a solidified stent to return to a liquid state).

Suitable biocompatible polymers include, for example, hydrogels, copolymers, and homopolymers. For example, modified cellulose and cellulosic derivatives (e.g., cellulose acetate) can be useful. A "modified cellulosic derivative" is a cellulosic polymer that is surface modified by covalently linking pendant biocompatible surface groups to the cellulosic substrate polymer, rendering it more biocompatible. Such surface groups can include those known in the art, such as, e.g., albumin.

The term "homopolymers" includes materials that also can be identified as slightly cross-linked homopolymers (i.e., they contain a relatively small amount of a second component either intrinsic in the production of the monomer or added purposely to insure enough cross-linking so as to protect the homopolymer from slowly dissolving away in an aqueous media such as blood). An example of such a homopolymer is hydroxyethyl methacrylate (HEMA).

With regard to hydrogels, suitable polymers either can be regular homopolymers containing substantially no other material in their matrices, or they can be copolymers prepared from two or more monomers such as, for example, styrene and vinyl acetate. In some cases, copolymer tailoring with various monomers can enhance the desirable properties of the biocompatible substance. Examples of monomers that can be copolymerized include, without limitation, hydroxyethyl methacrylate and glycidyl methacrylate.

Terpolymers also are useful in the methods described herein. Terpolymers are a subclass of copolymers in which three monomers are polymerized. An example of a useful terpolymer is glycidyl methacrylate/N-vinyl pyrrolidone/hydroxyethyl methacrylate (GMA/NVP/HEMA).

Other suitable materials that can be used to generate a stent as described herein include 2-polyhydroxyethyl methacrylate (2-P-HEMA), n-butyl cyanoacrylate (n-BCA), co-extrusions of poly(∈-caprolactone) and poly(ethylene oxide), cellulose acetates (e.g., cellulose diacetate), ethylene vinyl alcohol copolymers, hydrogels (e.g., acrylics), and polyacrylonitrile. In addition, copolymers (prepared with or without various additional monomers) and homopolymers can be polymerized from any of the following monomers: hydroxyalkyl acrylates and hydroxyalkyl methacrylates (e.g., hydroxyethyl acrylate, hydroxypropyl acrylate, and hydroxybutyl methacrylate), epoxy acrylates and epoxy methacrylates (e.g., glycidyl methacrylate), amino alkyl acrylates and amino alkyl methacrylates, N-vinyl compounds (e.g., N-vinyl pyrrolidone, N-vinyl carbazole, N-vinyl acetamide, and N-vinyl succinimide), amino styrenes, polyvinyl alcohols and polyvinyl amines made from suitable polymeric precursors, polyacrylamide and various substituted polyacrylamides, polysaccharides and modified polysaccharides, polyethylene glycol (PEG) and polypropylene glycol (PPG) based polymers, vinyl pyridine, vinyl sulfonate and polyvinyl sulfate, vinylene carbonate, vinyl acetic acid and vinyl crotonic acid, allyl amines and allyl alcohols, and vinyl glycidyl ether and allyl glycidyl ether. Processes and procedures for creating copolymers and/or homopolymers from the above monomers known in the art. These parameters are not critical to the presently products and methods provided herein, with the caveat that the final copolymer and/or homopolymer is non-toxic for animal (e.g., human) use.

Figure 5A:
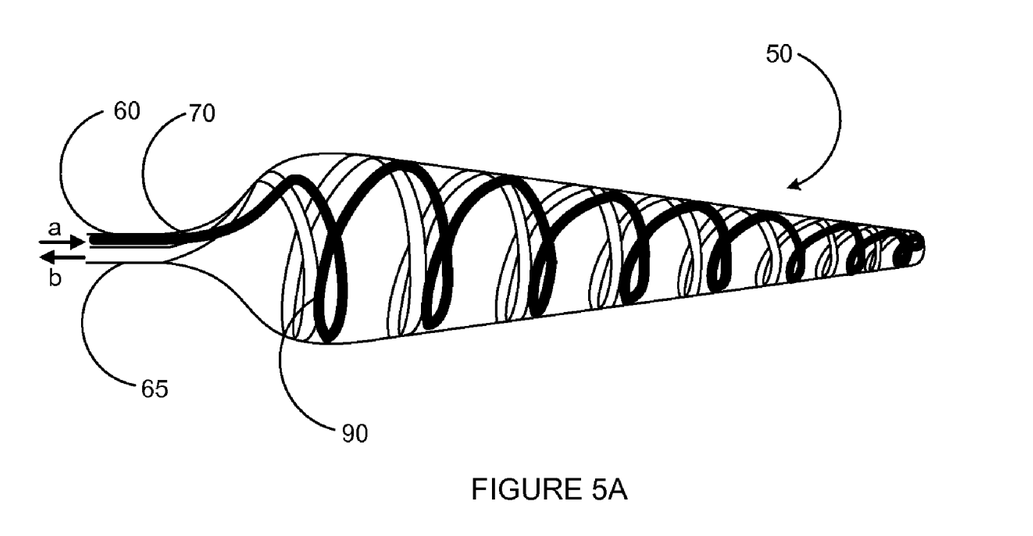
FIGS. 5A and 5B are drawings depicting another embodiment of a method as described herein.
Figure 5B:
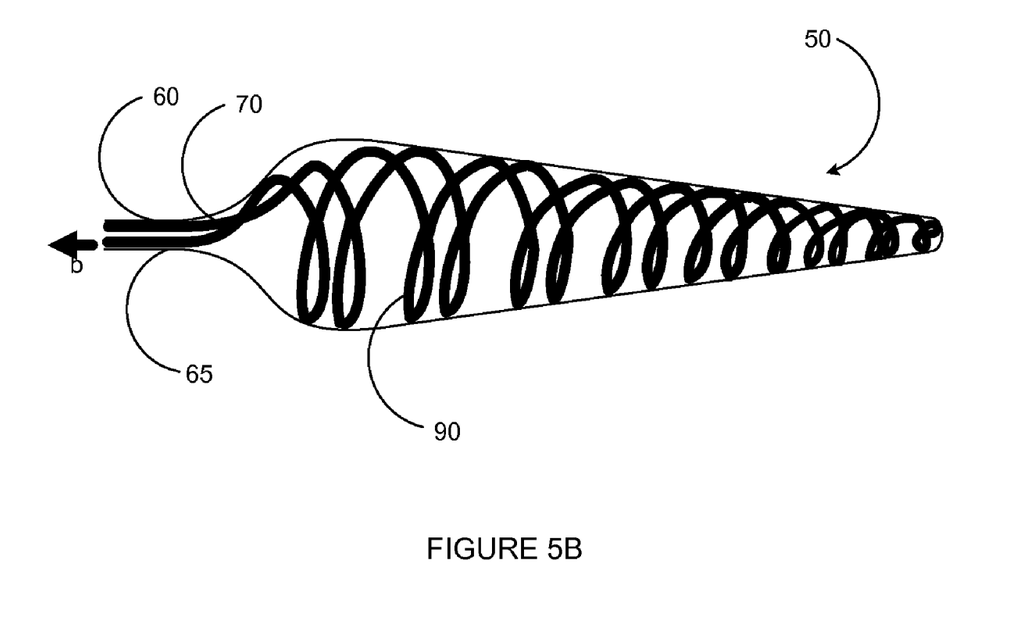

Any suitable device can be used to inject the stent material into the channel(s) on the exterior of the balloon. For example, an angioplasty catheter having a lumen in fluid communication with the groove(s) on a balloon surface can be used to transfer a liquid or gelatinous substance into the groove(s). Methods for making such catheters are well known in the art. In some embodiments, an injection device can have two ports that can be fluidly connected with the channel(s) on the balloon exterior. In such cases, the stent substance can be injected through one port into the channels or grooves on the balloon surface, and suction can be applied through a second port to facilitate delivery of the substance to the appropriate site. Such an embodiment is shown in FIGS. 5A and 5B, which depict stent substance 90 being injected through first port 60 into groove 70 on balloon 50. Suction applied at second port 65 can facilitate movement of substance 90 into and through groove 70. A timing algorithm can allow manipulation of the injection and suction parts of an injection apparatus. In some embodiments, there can be simultaneous injection at the first port and suction at the second port. Alternatively or in addition, injection at the first port can occur without suction at the second port, or vice versa, based on whether a complete scaffold is desired or whether a gap in the scaffold is desired at the site of a side branch to the vessel, for example. The injected substance can be radio opaque so that it is possible to visualize when the stent is in the appropriate location.

Figure 6:
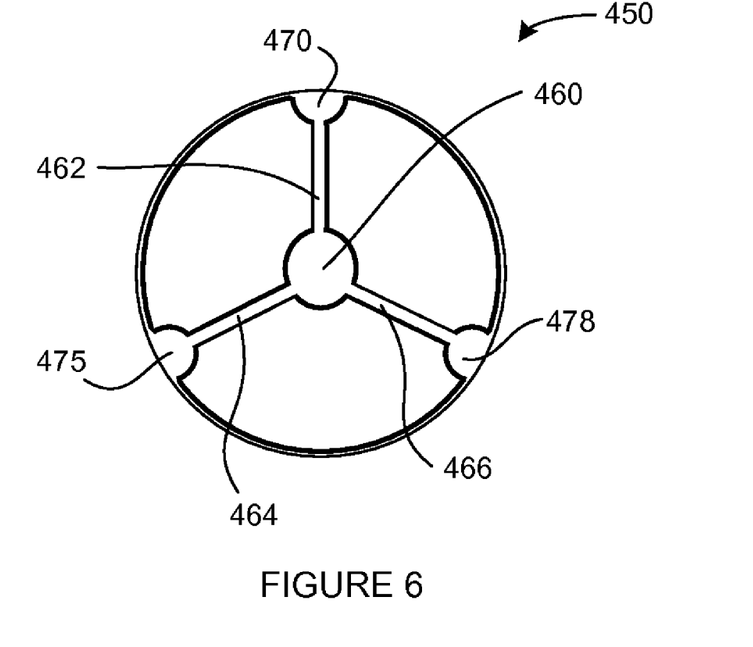
FIG. 6 is a drawing showing a cross-section through a balloon having a central injection port and side channels that are in fluid communication with the grooves in the exterior balloon wall.

In some embodiments, the channel(s) of a balloon can be pre-filled with a material that is liquid or gelatinous in form. Once the balloon is placed, whether the channels are pre-filled or filled after balloon placement, a "curing" agent can be injected to both inflate the balloon and solidify the liquid/gel. In some cases, this can be accomplished by having perforations and/or secondary tubes within the lumen of the balloon to allow the curing agent to interact with the liquid/gel. See, e.g., FIG. 6, which depicts a cross-sectional view of balloon 450 having central injection channel 460 and side channels 462, 464, and 466 extending to grooves 470, 475, and 478. A curing agent can be injected into central channel 460, and can reach the substance in grooves 470, 475, and 478 via side channels 462, 464, and 466. The fluid used to inflate balloon 450 can be hot or cold to activate the substance in grooves 470, 475, and 478, and/or to provide heating or cooling of the surrounding tissue to prevent injury. An electrode placed within a lumen of balloon 450 also can be used to provide heat or cold to cure the stent substance. In some embodiments, for example, a stent material can be cured by radiofrequency energy delivered to the material in grooves 470, 475, and 478.

Figure 7:
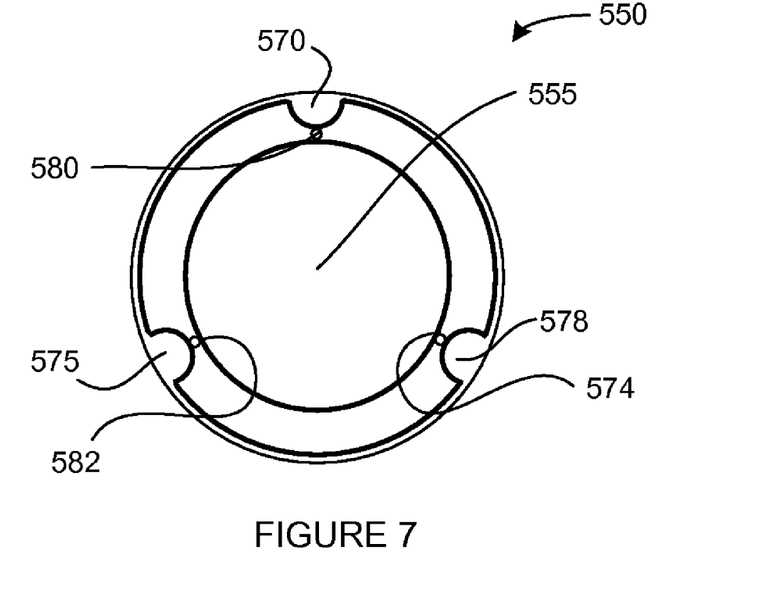
FIG. 7 is a drawing that depicts a cross-section of a balloon having a hollow central lumen extending therethrough, which can allow for continuous blood flow during stent placement.

In any of the methods provided herein, the substance used to form a stent can contain a radiopaque agent to allow for visualization of the stent during and after deployment. In some embodiments, the substance in the channels can contain a drug that can be eluted from the stent during and/or after placement. In addition, in some embodiments, a balloon can create a temporary lumen during deployment of the stent to allow for blood flow during the curing time. For example, a deployment balloon can assume a donut shape upon inflation, allowing blood flow through the center. See, e.g., FIG. 7, which shows a cross-sectional view of balloon 550 having central lumen 555 through which blood can flow, particularly after balloon 550 is inflated. A stent substance can be injected into grooves 570, 575, and 578 via injection channels 580, 582, and 584, for example.

Figure 8:
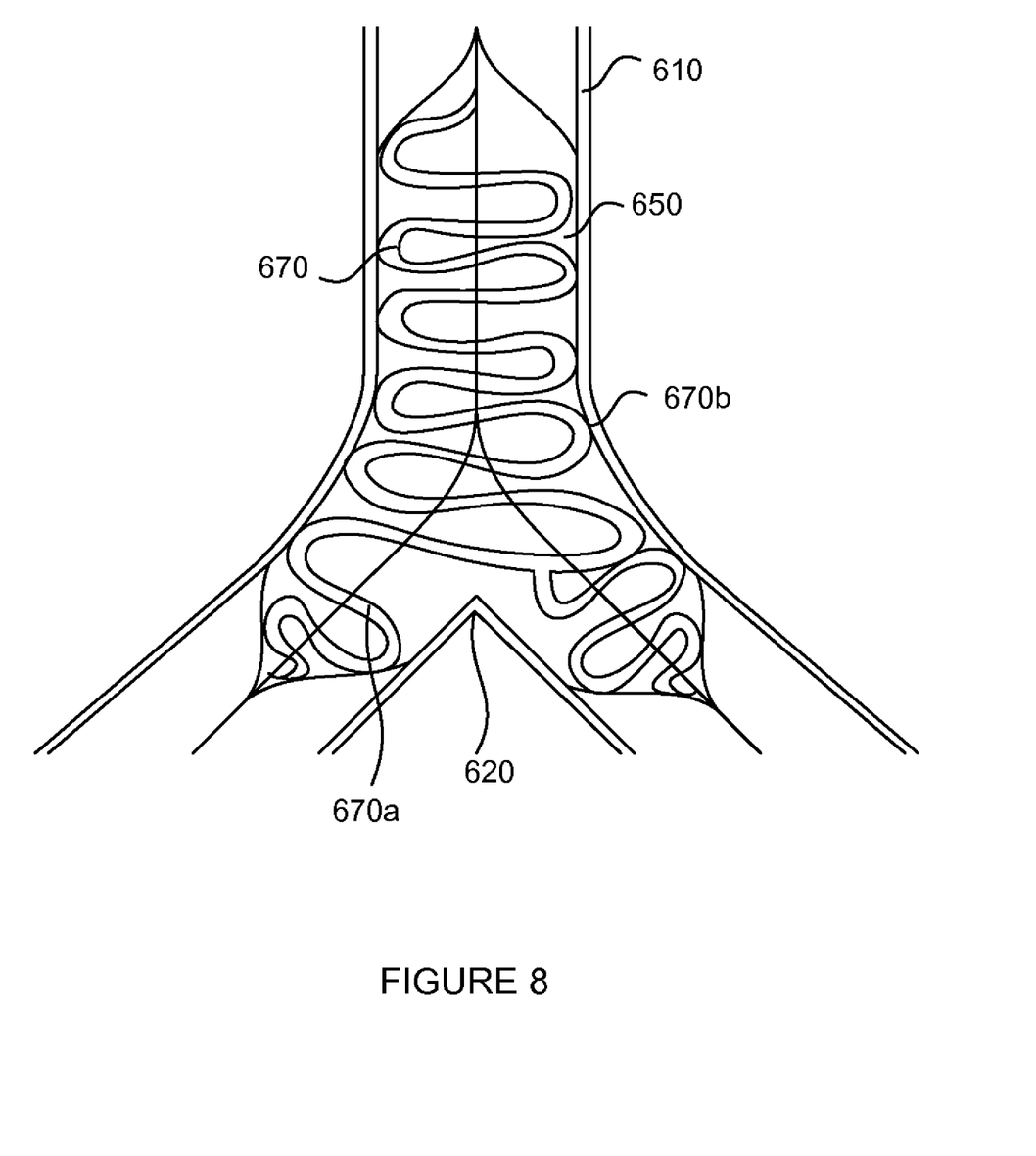
FIG. 8 is a drawing of a branched blood vessel having a bifurcated balloon positioned therein, such that a single stent can be generated in the main vessel and each of the side branches.

As discussed herein, the devices and methods provided in this document can be used in complex arterial lesions where the vessel diameter is not uniform, at sites proximal and/or distal to a site of stenosis, at bifurcating lesions, and at sites of complex stenosis at side branches, for example. See, for example, FIG. 8, which depicts branched balloon 650 inflated within vessel 610 at bifurcation 620. A fluid stent-forming substance can be injected along grooves 630, 630a, and 630b to generate a single bifurcated stent that can remain in place in main vessel 610 as well as in each branch just downstream of bifurcation 620.

In addition to their utility in complex arterial lesions, however, the stents provided herein can be placed in any uniform sized blood vessel. In some cases, a biologic/biocompatible "glue" can be injected along the channels of a balloon to provide a method for sealing off dissection flaps caused by angioplasty. In such situations, a "stent-like" scaffold may not be needed for long-term support of the vessel wall.

The stents and methods provided herein can also be useful in the complex cardiac venous anatomy to allow, for example, deployment of electrical charge (pacing) to stimulate the myocardium without stimulating extra cardiac structures. For such pacing and other iterations (e.g., branching lesions in an artery), a wire can be positioned within the scaffold using the injection port, or the material placed into the scaffold can be a conductor. The wire may simply help to hold the scaffold in place, or may be used as a conductor to be adapted. Thus, a stent scaffold as described herein can interface via wire to a high energy device (e.g., for ablation and/or defibrillation) placed in the subclavicular region, for example, with the wire (e.g., pacing leads) achieving a near perfect fit onto the myocardial surface from within irregularly shaped and branching second and third order cardiac vein branches. Other benefits with pacing from a conformable stent/scaffold include that capture of the phrenic nerve can be avoided, and that changes can be made to the resultant pacing vector without the need for multiple leads. In the central nervous system (e.g., venous branches), an additional benefit is that capture from pacing from the distal portion of a conformed stent can be ascertained by a recording electrode "created" on the proximal portion of the injected scaffold/stent.

To prevent extracardiac stimulation, a conformed stent can be placed in two steps. For example, once the balloon has been deployed in, e.g., the coronary venous system, markers can be placed on the balloon to orient the operator as to which side of the balloon is facing the myocardial tissue. The material that will make up the pacing stent can be injected such that the conducting material will face the myocardial surface, and an insulator can be injected to face the extracardiac surface. This can allow for high output stimulation without extracardiac capture, and can be done using a timing algorithm that allows injection based on the knowledge of how much material should be injected to fill a certain portion of the stent. Alternatively, a stent can be generated by injection in two sections, for example, when the stent scaffold itself is etched into the balloon with two separate lumens for injection. For example, when the balloon is in the coronary sinus branch, one hemi-cylinder (e.g., the hemi-cylinder facing the myocardial wall) can have a groove for the pacing stent and the other hemi-cylinder can have a groove for injecting the insulating material. The resulting stent can be nearly a single structure, but current from the battery can go only to the hemi-cylinder facing the myocardial wall.

The materials and methods provided herein also can be used to generate uniquely shaped and sized pacing leads for stimulating devices placed in the central nervous system (e.g., brain and spinal chord), as well as in the vasculature of other organs, including blood vessels draining or supplying muscle, peripheral nerves, dorsal root, and ganglia, where standard placement of a preshaped stent would be difficult.

Stents and wires used for such pacing applications can contain, e.g., titanium, platinum, and other conductors commonly used to create electrodes. In addition, other dielectrics can be used, including those engineered at a monomolecular level to prevent thrombus formation or to allow transmission of direct current in addition to radiofrequency energy.

Further, the stents and methods described herein can be useful for other extravascular applications. For example, a stent provided herein can be deployed in the gastrointestinal tract (e.g., bile duct, bowels, or urinary tubes), and can be used for anastamosis (e.g., in bypass grafts). An electrically conductive stent material in the heart, brain or periphery also may function as a sensor to detect normal or abnormal electrical activity. Such a sensor can be coupled via various means to an "effector" mechanism to generate a neuro-muscular or biologic response at a remote site.

For airway protection applications, a conformable stent can be applied in the trachea and/or bronchus, as well as in the posterior pharynx and nasopharynx. Such methods can be used for treatment of narrowing of the airways and dynamic airway obstruction, such as can occur with sleep apnea and nasopharyngeal obstructions. In such embodiments, a standard stent likely would be difficult to place for various reasons, including the complex geometry of this region. A balloon placed via the nostrils or the pharynx can take the shape of these complex structures, and a conformable stent with gaps left in place for the areas above the soft palates can prevent dynamic compromise of these structures, preventing obstruction. Similarly, tracheal stenosis or bronchial stenosis can be treated with balloon tracheo/bronchoplasty, followed by placement of a conformable stent as described herein.

Conformable stents also can be useful in the biliary tract, the intestinal tract, and the salpingo-uterine system, for example. Like the airway, the biliary tract has a complex, branched anatomy. A stent as provided herein can be used, for example, to treat branch lesions and biliary stenosis, including at second and third order branches of the biliary system. In the intestinal tract, a stent as provided herein also can be used at areas of stenosis that are associated with complex geometry. For example, a stent can be placed at the region of the ileocecal junction, which can be affected in disorders such as ulcerative colitis and Crohn's disease. Placing a stent in such a location via an endoscope typically is difficult because of the disparity in lumen size between the cecum and the ileum. A conformable balloon can take the shape of the respective lumens and allow placement of a conformable stent. In the salpingo-uterine system, a stent as provided herein can be used to treat stenosis associated with infertility, for example. Embodiments that allow elusion of a drug may be particularly useful at such sites.

The conformable stents provided herein also can be used to create varying degrees of penile tumescence. A stent can be created around a balloon and placed in one of the main dorsal or central penile veins. Such a stent may be most similar to the pacing stents described herein. The stent itself, through a conductor, can be attached to a small battery-powered generator that can be placed subcutaneously in anatomic proximity. The material of the stent can be such that the application of a charge will create variation in the sides and physical state of the stent (similar to "curing" with heat, cooling, RF, or DC current, for example). Such a device can be used for treatment of erectile dysfunction by relatively and reversibly occluding the penile vein while opening the arterial vasculature. The generator can be placed subcutaneously, and an external communicating device can be used to control the device.

The technology described herein allows for creation of stents that are useful not only for stenosis in lumenal structures, but also outside lumenal structures. In some instances, compression of a structure or obliteration of a lumen of a particular structure may be required. In such instances, because the structure itself is large, percutaneous or laparoscopic deployment of a compression stent large enough to allow the device to completely engulf the structure before it compresses the structure can be nearly impossible, and thus may require an open surgical procedure.

Since balloons are expandable, and the stents provided herein are created on balloons, deployment of a compression stent from a rather small opening into the body (e.g., a venotomy, atriotomy, skin incision, or subxiphoid incision) is now possible. Essentially, a balloon to be deployed can itself be a hollow cylinder. That is, two concentric layers of balloon material can form a cylinder having a hollow center. Such a balloon can be introduced over a wire or sheath into the structure requiring compression or obliteration. Once introduced and positioned within the body as desired, the balloon can be expanded. The structure to be compressed then can be placed inside the hollow portion of cylindrical balloon. The stent can be formed on the inner layer of the balloon around the partially compressed anatomic structure. The stent itself can have characteristics that cause it to compress or become smaller. When the balloon is deflated, the stent can be left in place, allowing it to further obliterate the structure required. Areas where such an approach can be useful include occlusion of vessels that may be thrombogenic, pouches, appendages, appendices, and aneurysmal sites that may require partial obliteration.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method for making a stent, comprising:
 a) inserting into a bodily vessel a balloon having a wall with an outer surface that defines one or more preformed grooves, or having a wall containing one or more preformed channels, wherein the preformed grooves or channels are configured to form a scaffold for a stent;
 b) inflating the balloon at the site of a stenosis within the vessel such that the balloon contacts the vessel wall along the site of the stenosis;
 c) injecting a fluid substance into the one or more preformed grooves or channels, wherein the balloon remains in contact with the vessel wall throughout the injecting step;
 d) allowing the fluid substance to harden; and
 e) deflating the balloon and removing it from the vessel.
2. The method of claim 1, wherein the one or more preformed grooves or channels are configured to form a mesh pattern scaffold for a stent.
3. The method of claim 1, wherein the one or more preformed grooves or channels are configured to form a helical or coiled scaffold for a stent.
4. The method of claim 1, wherein the one or more preformed grooves or channels are configured to form a scaffold of connected rods for a stent.
5. The method of claim 1, wherein the outer surface of the balloon and the surface of the one or more preformed grooves have a covering that is separate from the balloon wall.
6. The method of claim 5, wherein the balloon wall and the covering comprise different materials.
7. The method of claim 5, wherein the balloon wall and the covering comprise the same materials.
8. The method of claim 1, wherein each of the one or more preformed grooves has a separate covering, wherein each of the separate coverings defines a lumen extending along the outer surface of the balloon.
9. The method of claim 8, wherein each of the one or more channels has a triangular cross-section.
10. The method of claim 1, wherein the injected substance is selected from the group consisting of hydrogels, homopolymers, and copolymers.
11. The method of claim 1, wherein the injected substance is selected from the group consisting of modified cellulose, cellulosic derivatives, and polymers of hydroxyethyl methacrylate, glycidyl methacrylate, glycidyl methacrylate/N-vinyl pyrrolidone/hydroxyethyl methacrylate, 2-polyhydroxyethyl methacrylate, n-butyl cyanoacrylate, co-extrusions of poly(∈-caprolactone) and poly(ethylene oxide), cellulose acetates, ethylene vinyl alcohol copolymers, acrylics, polyacrylonitrile, hydroxyalkyl acrylates, hydroxyalkyl methacrylates, epoxy acrylates, epoxy methacrylates, amino alkyl acrylates, amino alkyl methacrylates, N-vinyl compounds, amino styrenes, polyvinyl alcohols, polyvinyl amines, polyacrylamide, polysaccharides, modified polysaccharides, polyethylene glycol, polypropylene glycol, vinyl pyridine, vinyl sulfonate, polyvinyl sulfate, vinylene carbonate, vinyl acetic acid, vinyl crotonic acid, allyl amines, allyl alcohols, vinyl glycidyl ether, and allyl glycidyl ether.

12. The method of claim 1, wherein the injected substance hardens at bodily temperature.

13. The method of claim 1, further comprising injecting a curing agent.

14. The method of claim 1, wherein the site of the stenosis is located in a vessel with non-uniform diameter, at an arterial branch point, at an ostium of a branch of a main vessel, or in a vessel at a site of multiple branching.

15. The method of claim 1, further comprising positioning a wire within the one or more preformed grooves or channels via the injection port.

16. The method of claim 1, wherein the fluid material comprises a conductor.

17. The method of claim 16, wherein the conductor comprises titanium or platinum.

* * * * *